(12) United States Patent
Cork

(10) Patent No.: US 9,919,092 B2
(45) Date of Patent: Mar. 20, 2018

(54) OPTICAL DETECTION OF LIPIDS

(71) Applicant: Fenwal, Inc., Lake Zurich, IL (US)

(72) Inventor: William Henry Cork, Mettawa, IL (US)

(73) Assignee: Fenwal, Inc., Lake Zurich, IL (US)

(*) Notice: Subject to any disclaimer, the term of this patent is extended or adjusted under 35 U.S.C. 154(b) by 0 days.

(21) Appl. No.: 15/455,289

(22) Filed: Mar. 10, 2017

(65) Prior Publication Data

US 2017/0182239 A1    Jun. 29, 2017

Related U.S. Application Data

(62) Division of application No. 14/114,577, filed as application No. PCT/US2012/071896 on Dec. 28, 2012, now abandoned.
(Continued)

(51) Int. Cl.
| | |
|---|---|
| *C02F 1/00* | (2006.01) |
| *A61M 1/34* | (2006.01) |
| *A61M 1/36* | (2006.01) |
| *G01N 21/59* | (2006.01) |
| *G01N 33/49* | (2006.01) |

(52) U.S. Cl.
CPC ........ *A61M 1/3496* (2013.01); *A61M 1/3693* (2013.01); *G01N 21/59* (2013.01); *G01N 33/491* (2013.01); *A61M 2202/08* (2013.01); *A61M 2205/3313* (2013.01)

(58) Field of Classification Search
None
See application file for complete search history.

(56) References Cited

U.S. PATENT DOCUMENTS

| | | |
|---|---|---|
| 4,227,814 A | 10/1980 | Soodak |
| 5,135,667 A | 8/1992 | Schoendorfer |

(Continued)

FOREIGN PATENT DOCUMENTS

| | | |
|---|---|---|
| WO | WO96/17243 | 6/1996 |
| WO | WO00/77494 A1 | 12/2000 |

OTHER PUBLICATIONS

International Search Report and Written Opinion for PCT Patent Appl'n. No. PCT/US2012/071896, dated Apr. 8, 2013.
(Continued)

*Primary Examiner* — Richard Gurtowski
(74) *Attorney, Agent, or Firm* — Cook Alex Ltd.

(57) ABSTRACT

Blood separation systems and methods are provided for detecting lipids in plasma that has been separated from a plasma-containing fluid, such as blood. Plasma is separated from a fluid in a blood separator, with at least a portion of the separated plasma being removed from the blood separator via a plasma flow path. Blue and/or ultraviolet light is passed through the separated plasma in the blood separator or in the plasma flow path, with at least a portion of the light being received after passing through the separated plasma. A signal is generated based on the amount of light passing through the separated plasma, with the signal being indicative of the lipid content of the separated plasma. Determining the lipid content of the separated plasma involves comparing the difference between the signal and a reference signal that represents receipt of all or a pre-selected amount of the light.

18 Claims, 7 Drawing Sheets

Related U.S. Application Data

(60) Provisional application No. 61/677,123, filed on Jul. 30, 2012.

(56) References Cited

U.S. PATENT DOCUMENTS

| | | | |
|---|---|---|---|
| 5,194,145 | A | 3/1993 | Schoendorfer |
| 5,316,667 | A | 5/1994 | Brown et al. |
| 5,632,893 | A | 5/1997 | Brown et al. |
| 5,868,696 | A | 2/1999 | Giesler et al. |
| 6,312,607 | B1 | 11/2001 | Brown et al. |
| 6,582,350 | B2 | 6/2003 | Dolecek |
| 7,906,771 | B2 | 3/2011 | Carter |
| 2002/0128584 | A1 | 9/2002 | Brown et al. |
| 2003/0123047 | A1 | 7/2003 | Pettersson |
| 2003/0151819 | A1* | 8/2003 | Pong .............. B82Y 20/00 359/582 |
| 2005/0260175 | A1 | 11/2005 | Hedrick et al. |
| 2009/0129976 | A1 | 5/2009 | Hoshino et al. |
| 2009/0211962 | A1 | 8/2009 | Min et al. |
| 2010/0025336 | A1 | 2/2010 | Carter |
| 2012/0199539 | A1 | 8/2012 | Foley |

OTHER PUBLICATIONS

"What Wavelength Goes With a Color?", May 9, 2009, NASA, "Blue Light," https://web.archive.org/web/20090509232245/http://science-edu.larc.nasa.gov/EDDOCS/Wavelengths_for_Color.

* cited by examiner

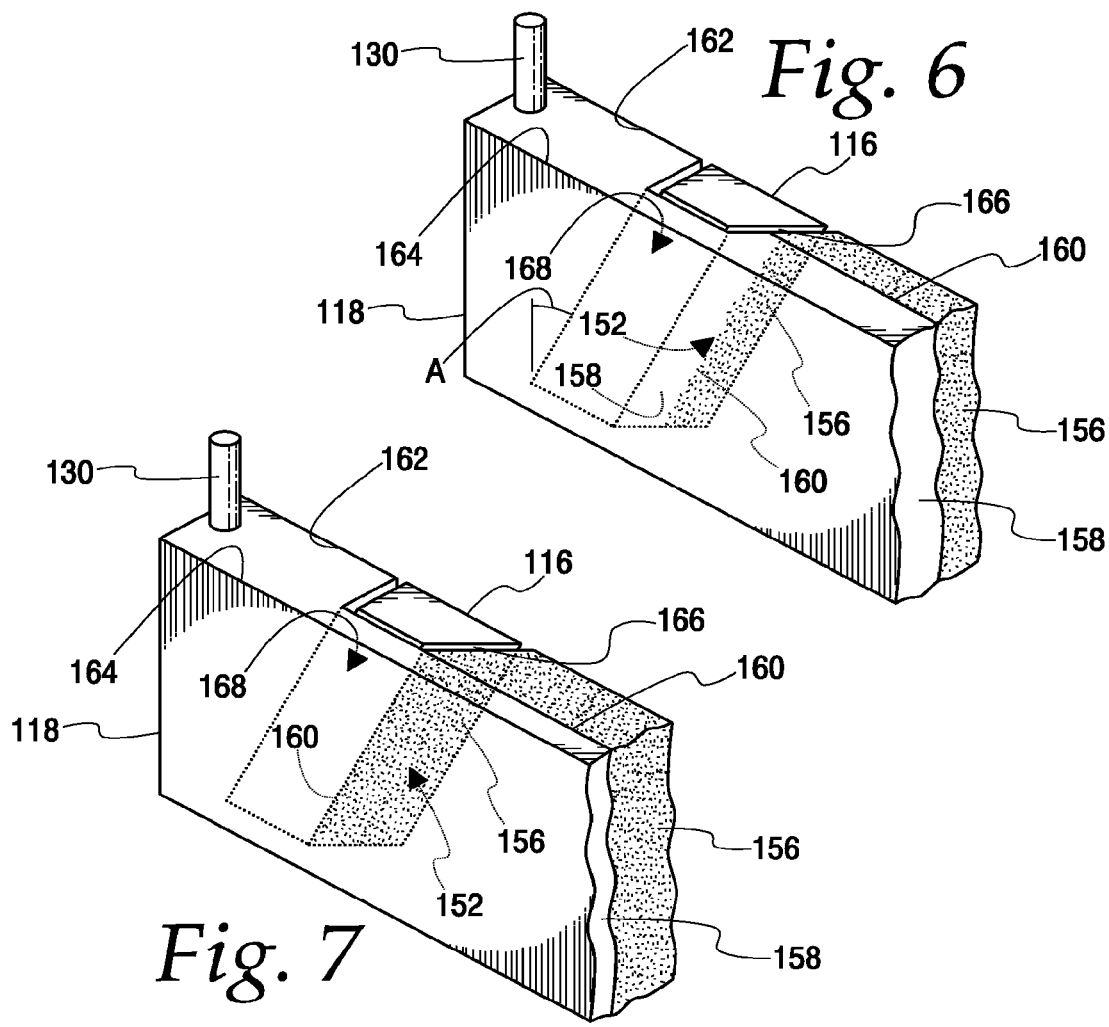
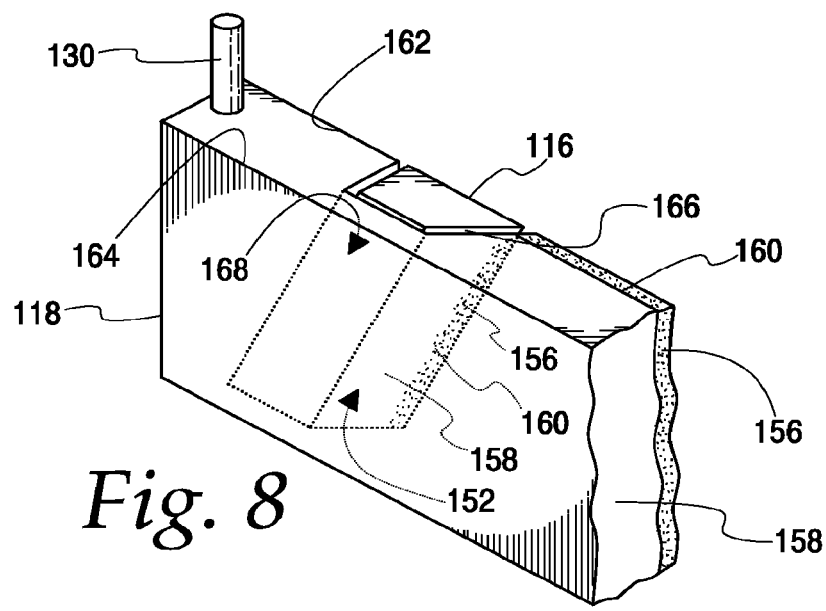

OPTICAL DETECTION OF LIPIDS

RELATED APPLICATION

This application is a divisional of U.S. patent application Ser. No. 14/114,577, filed Oct. 29, 2013, which is a U.S. national stage application of PCT Patent Application No. PCT/US12/71896, filed Dec. 28, 2012, which claims the benefit of and priority of U.S. Provisional Patent Application Ser. No. 61/677,123, filed Jul. 30, 2012, the contents of each of the above applications being incorporated by reference herein.

TECHNICAL FIELD

The invention relates to blood separation systems and methods. More particularly, the invention relates to systems and methods for detecting lipids in separated blood plasma.

BACKGROUND

Various blood processing systems now make it possible to collect particular blood constituents, instead of whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., which is an affiliate of Fresenius Kabi AG of Bad Homburg, Germany, or other centrifugal separation devices, or a spinning membrane-type separator, such as the AUTOPHERESIS-C® device from Fenwal, Inc.

In some of these systems, an optical device is provided for detecting the presence of hemoglobin in separated blood plasma. However, experience has shown that the presence of excessive lipids in the plasma may result in false hemoglobin alarms, due to the nature in which the optical device detects the presence of hemoglobin and difficulty that results in distinguishing hemoglobin from lipids. The presence of excessive lipids in plasma can also create difficulties in systems which attempt to quantify platelets being removed in plasma from a blood separator or which attempt to monitor the location of the interface between separated red cells and plasma during centrifugal separation. Accordingly, the need remains for a blood processing system which can better detect the presence of lipids in separated plasma.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an optical sensor system is provided for use in combination with a blood separation chamber having a plasma flow path for the flow of separated plasma. The optical sensor system includes a blue and/or ultraviolet light source configured to pass a blue and/or ultraviolet light through plasma in the plasma flow path. The optical sensor system also includes a light detector configured to receive at least a portion of the blue and/or ultraviolet light and generate a signal indicative of lipid content in the plasma in the plasma flow path.

In another aspect, a blood processing system comprises a blood separator with a fluid processing region, which is configured to separate plasma from blood. The system also includes a plasma flow path communicating with the fluid processing region for removing plasma therefrom. An optical sensor system of the blood processing system includes a blue and/or ultraviolet light source configured to pass a blue and/or ultraviolet light through separated plasma in the plasma flow path. The optical sensor system also includes one or more light detectors configured to receive at least a portion of the blue and/or ultraviolet light and generate a signal indicative of lipid content in the separated plasma.

In one aspect, a method is provided for separating blood into plasma and other blood components. The method includes separating plasma from blood in a blood separator. At least a portion of the separated plasma is removed from the blood separator via a plasma flow path, and a blue and/or ultraviolet light is passed through the separated plasma in the blood separator or in the plasma flow path. At least a portion of the blue and/or ultraviolet light is received after passing through the separated plasma and a signal is generated based on the amount of blue and/or ultraviolet light passing through the plasma. The signal is indicative of lipid content in the separated plasma. The lipid content of the separated plasma is determined by comparing the difference between the signal and a reference signal representing receipt of all or a pre-selected amount of the blue and/or ultraviolet light, with an output that is indicative of the lipid content in the separated plasma being generated.

BRIEF DESCRIPTION OF THE DRAWINGS

FIG. 6 is an enlarged perspective view of an interface ramp carried by the centrifuge assembly in association with the blood separation chamber, showing the centrifugally separated red blood cell layer, plasma layer, and interface within the chamber when in a desired location on the ramp;

FIG. 7 is an enlarged perspective view of the interface ramp shown in FIG. 6, showing the red blood cell layer and interface at an undesired high location on the ramp;

FIG. 8 is an enlarged perspective view of the interface ramp shown in FIG. 6, showing the red blood cell layer and interface at an undesired low location on the ramp;

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
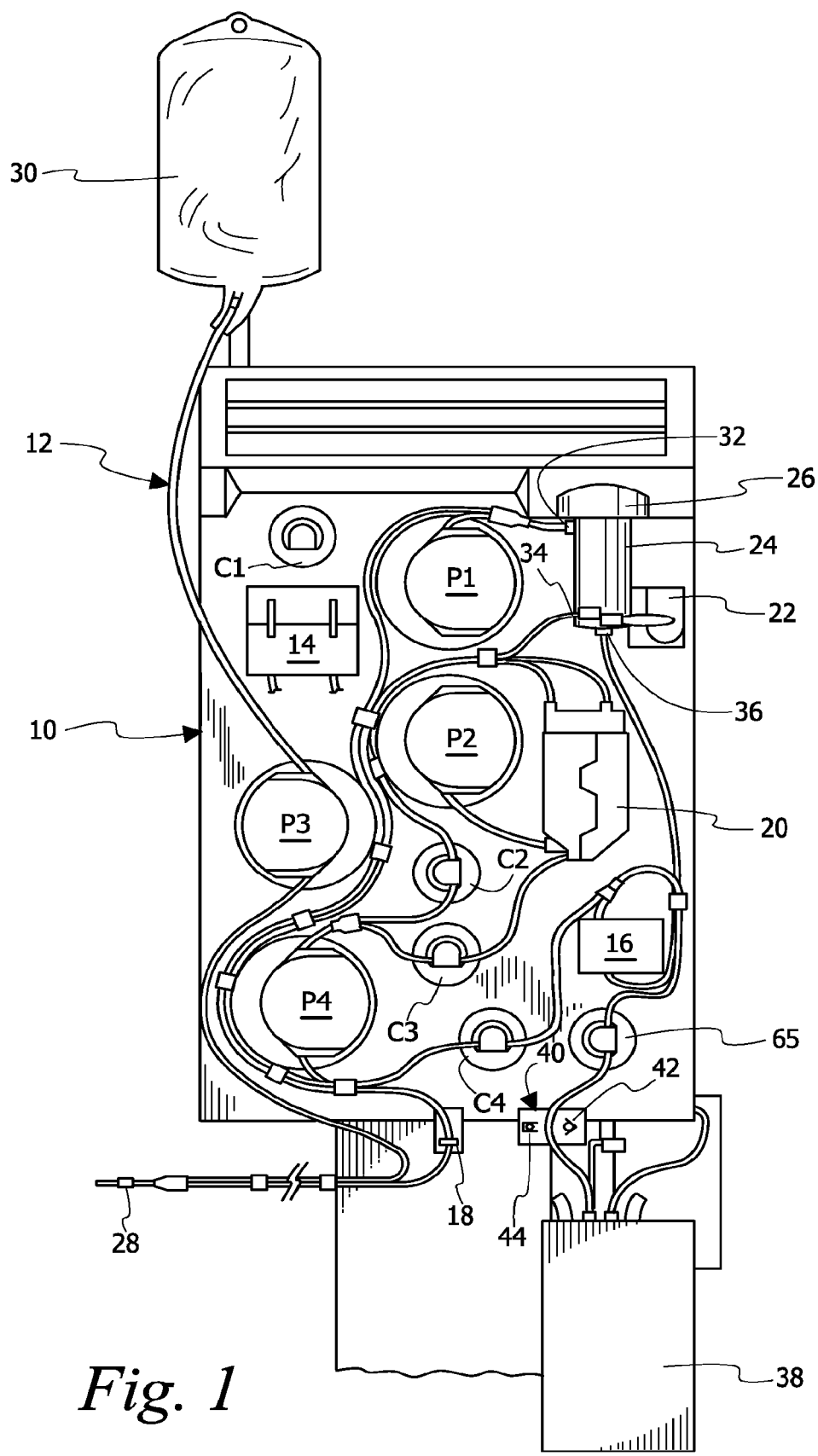
FIG. 1 is a front elevational view of a blood processing system employing aspects of the present disclosure, in combination with a disposable fluid set having a spinning membrane-type blood separation chamber.

FIG. 1 shows a spinning membrane-type blood processing system 10 of the type currently marketed as the AUTOPHERESIS-C® device by Fenwal, Inc. The system 10 of FIG. 1 is merely exemplary of one type of blood processing system with which the apparatus and methods of the present disclosure may be employed, and it should not be understood as limiting the applicability of the present disclosure.

The system 10 is provided with various pumps, detectors, clamps, and the like, under control of a microprocessor or controller, for cooperation with a disposable fluid set 12. As illustrated in FIG. 1, there are provided pumps P1-P4 on the front face of the system 10. These pumps may be of the peristaltic type and cooperate with the various tubing of the disposable fluid set 12 to flow blood in the desired directions between the various elements of the set 12.

A series of clamps C1-C5 may also be provided to receive various tubing of the disposable fluid set 12. The clamps C1-C5 are movable between open or closed positions and thus operate to open or close the tubing associated therewith.

The face of the system 10 may include a number of other components, such as a pressure transducer 14, a hemoglobin detector 16, an air detector 18, sensors for determining the levels of liquid in reservoir 20, and a mount or lower holder 22 for a blood separation chamber 24 of the disposable fluid set 12. The face of the system 10 may also include a motor cup or rotation actuator 26 for mounting motor magnets which, in turn, drive rotors of the separation chamber 24. Thus, the separation chamber 24 may be installed on lower mount 22 with its upper end in the rotation actuator 26, whereby magnetic connection is effected between the magnetic drive motor and the rotor of the installed chamber.

In accordance with a method of separating blood into constituent parts using the illustrated system 10 and set 12, the set 12 is attached to the system 10, as shown in FIG. 1, with its tubing running through the various pumps, clamps, and detectors. Under control of the microprocessor, the system 10 operates the pumps, clamps, detectors and the like to draw blood from a blood source (e.g., a donor or a patient or a container) into the set 12 via an access device 28, such as a phlebotomy needle. Anticoagulant from an anticoagulant source or container 30 of the set 12 may be added to the blood under operation of one or more of the pumps. The anticoagulated blood is directed into an upper port 32 of the spinning membrane-type separation chamber 26, which defines a fluid processing region in which the blood is separated into plasma and cellular blood components. Additional details of a suitable separation chamber and its operation may be found in U.S. Pat. Nos. 5,135,667 and 5,194,145, which are incorporated herein by reference.

The separated cellular components may exit the separation chamber 26 via port 34 and flow into the reservoir 20. The separate cellular components may be stored for later use or processing or may be returned to the blood source via the access device 28.

The separated plasma may exit the separation chamber 26 via port 36 and associated plasma flow path or plasma line of the set 12 to flow through the hemoglobin detector 16 before entering a plasma storage container 38. In one embodiment, the hemoglobin detector 16 may comprise a light source and a light detector, with the light source being configured to emit a green light having a wavelength in the range of about 550-580 nm. Hemoglobin will absorb such light, meaning that a low level reading by the light detector (i.e., when an amount of the green light is absorbed by the plasma in the plasma flow path instead of passing through it) is indicative of a greater hemoglobin concentration or content in the separated plasma. The light detector generates a signal indicative of the hemoglobin concentration or content in the plasma and transmits it to the controller of the system 10, which may generate an alarm or signal to alert an operator to an elevated hemoglobin concentration or content in the separated plasma, should the level exceed a certain amount, and/or change relevant pump speeds to alter the processing conditions to reduce hemolysis.

In accordance with the present subject matter, in addition to flowing through the hemoglobin detector 16, the separated plasma may also flow through a lipid detector or optical sensor system 40. In the illustrated embodiment, the lipid detector 40 is located downstream of hemoglobin detector 16, but it may be located upstream of the hemoglobin detector 16 in other embodiments, or the hemoglobin and lipid detectors may be incorporated into a single integrated detector unit or station.

The lipid detector 40 includes one or more light sources 42 and one or more light detectors 44 positioned and oriented to receive at least a portion of light emitted by the light source(s). For example, in one embodiment, each light source includes an associated light detector on the opposite side of the disposable set tubing passing through the lipid detector 40. In other embodiments, the light detectors may be positioned at an angle with respect to the associated light sources and/or there may be a different number of separate light sources and light detectors, and they may be integrated together as well.

Each light source 42 shines light through the tubing, to be at least partially received by the associated light detector(s) 44. Depending on the nature of the light and the composition of the fluid passing through the tubing, not all of the light emitted by the light source(s) may be received by the associated light detector(s). For example, certain wavelengths of light will be absorbed by certain fluid constituents, rather than passing therethrough and being detected. Accounting for other factors (e.g., the tendency of light passing through the tubing to be scattered or absorbed by the tubing itself), the percentage and nature of light that is received by a light detector is indicative of the percentage of light (or at least one or more wavelengths thereof) absorbed by the fluid or a component thereof.

As noted above, the presence of lipids in separated plasma may be problematic for a number of reasons, including false hemoglobin alarms from certain hemoglobin detectors, difficulties in quantifying platelets present in the separated plasma, and the possible miscalculation of the location of the interface between separated red cells and plasma during centrifugal separation. Accordingly, the detection of lipids in separated plasma, and particularly the differentiation of lipids from hemoglobin, would be very useful. Hemoglobin substantially absorbs light at approximately 550 to 580 nm (depending on its oxygen content), while substantially allowing the transmission of light at other wavelengths, including blue light (having a wavelength of approximately 470 nm, for example, or in the range of approximately 450 to 510 nm) and ultraviolet light (having a wavelength of approximately 380 nm, for example, or in the range of approximately 300 to 400 nm). On the other hand, blue and/or ultraviolet light will be substantially absorbed by lipids present in the separated plasma flowing through the tubing. Thus, a light source 42 configured to emit blue and/or ultraviolet light may be used to detect lipid presence or absence in plasma.

In the embodiment of FIG. 1, at least a single light source 42 is preferably employed, which may direct blue light, ultraviolet light, or a light containing both wavelengths through the tubing and plasma flowing therethrough. In other embodiments, a plurality of light sources may be employed, each of which may direct blue light, ultraviolet light, or a light containing both wavelengths through the tubing and plasma flowing therethrough. If a plurality of light sources is employed, the various light sources may emit the same light or light at different wavelengths. The nature of the light source(s) may vary without departing from the scope of the present disclosure, but in one embodiment the light sources comprise light-emitting diodes.

The blue and/or ultraviolet light passes through the tubing and plasma flowing through the tubing, and is at least partially received by the associated light detector(s) 44. The light detector or detectors (which may comprise photodiodes in one embodiment) generate a signal that is indicative or representative of the amount or concentration of lipids in the plasma. That signal may, if needed, be further processed by a processor of the lipid detector 40 or the controller. If a relatively large amount or percentage of the light is received by the detector(s), a larger or stronger signal may be generated by the detector(s). If a relatively small amount or percentage of the light is received by the detector(s), a smaller or weaker signal may be generated by the detector (s). The smaller or weaker the signal, the more lipids are present in the separated plasma flowing through the tubing, and consequently the more blue and/or ultraviolet light has been absorbed. If a plurality of light detectors is employed, a plurality of signals may be generated by the light detectors (e.g., with each light detector generating one signal) or the readings taken by the various light detectors may be aggregated into a single signal.

The processor or processing element receives the signal(s) from the light detector(s) that is reflective of the lipid content of the separated plasma for further analysis. This analysis may be carried out by the processing element in any of a variety of ways. In one embodiment, the processing element compares the signal(s) from the light detector(s) to an expected or reference signal or value, which represents a signal generated by the light detector(s) upon receiving all or a pre-selected amount of light from the light source(s). The difference between the actual signal(s) and the expected signal is indicative of the lipid content or concentration of the separated plasma, with a relatively small difference indicating an absence or relatively small amount of lipids and a relatively large difference indicating the presence of a relatively great amount of lipids in the plasma. Other factors (e.g., the effect of the plasma and tubing on the transmission of light from the light sources to the light detectors) may be considered by the processing element when analyzing the signal(s) from the light detector(s).

After analyzing the signal(s), the processing element generates an output indicative of the lipid content or concentration of the plasma in the tubing. With this output, the controller of the system 10 may generate an alarm or signal to alert an operator to the presence of lipids in the separated plasma, should the level exceed a certain amount. For example, an average or "normal" lipid concentration value may be approximately 100 mg/dL. On the other hand, a lipid concentration greater than that or at a particular threshold (e.g., approximately 200 mg/dL in one embodiment) may be considered elevated or "high" and, if detected, would register an alarm or generate an output indicative of lipemic plasma. In one example, it was found that approximately 28-38% of blue light having a wavelength of approximately 490 nm shining into plasma with a lipid concentration of approximately 100 mg/dL was absorbed or otherwise not transmitted to the associated light detector. In contrast, approximately 58-62% of the same blue light shining into plasma with a lipid concentration of approximately 200 mg/dL was absorbed or otherwise not transmitted to the associated light detector. Thus, based on such an example, the controller or processor of the system 10 may be configured to generate an alarm when more than 40% or more than 50% of the light emitted by the light source is absorbed or otherwise not transmitted to the associated light detector. Lipemic plasma may be unsuitable for certain therapeutic uses, but suitable for other uses. Accordingly, any plasma that is identified by the lipid detector 40 as lipemic may be labeled, segregated, or otherwise earmarked for uses in which it is suitable.

In one embodiment, the lipid detector 40 may be employed in connection with the operation of the hemoglobin detector 16, such that it will only be actuated by the system controller to analyze the separated plasma if hemoglobin is detected. If the lipid detector detects the presence of a significant amount of lipids in the plasma, it may tend to indicate that the hemoglobin detector is generating a false alarm due to difficulty in distinguishing lipids from hemoglobin. In order to decrease the number of false hemoglobin alarms, the controller of the system 10 may be configured to await signals from the lipid detector 40 and the hemoglobin detector 16 prior to generating a hemoglobin alarm or signal. If plasma passing through the plasma flow path is determined by the detectors to have high levels of both hemoglobin and lipids, the controller may be configured to cancel the hemoglobin signal alert and only generate a lipid signal or alert, thereby avoiding a false hemoglobin alarm. Thus, such a system helps to prevent false alarms whereby lipemic plasma is erroneously identified as hemolytic plasma by the hemoglobin detector 16. In other embodiments, the lipid detector 40 may be independent of the hemoglobin detector 16 and operate regardless of whether the hemolysis is detected in the plasma by the hemoglobin detector 16.

Figure 2:
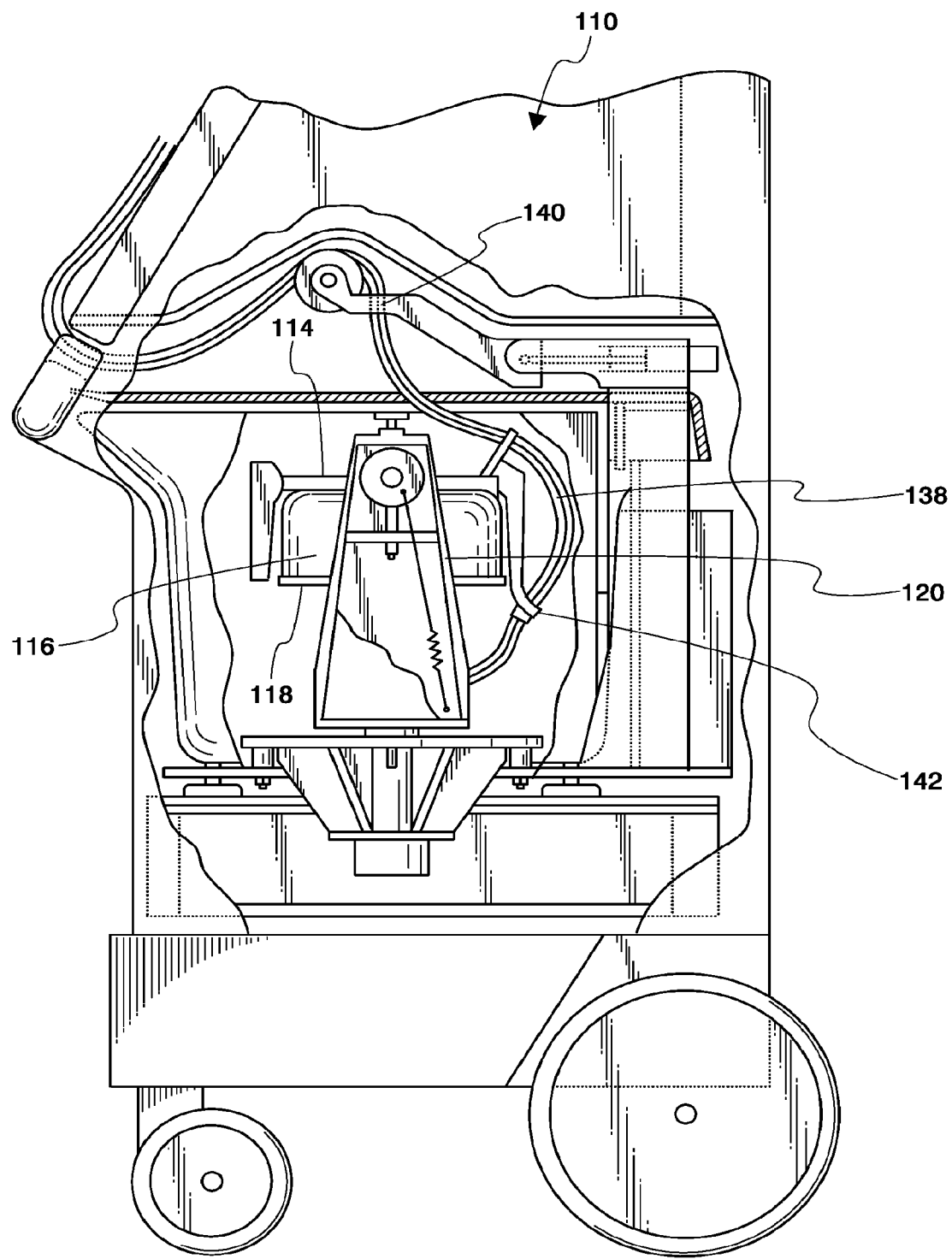
FIG. 2 is a side elevational view, with portions broken away and in section, of a blood processing system employing aspects of the present invention, with a centrifuge bowl and spool of the system being shown in their operating position.
Figure 3:
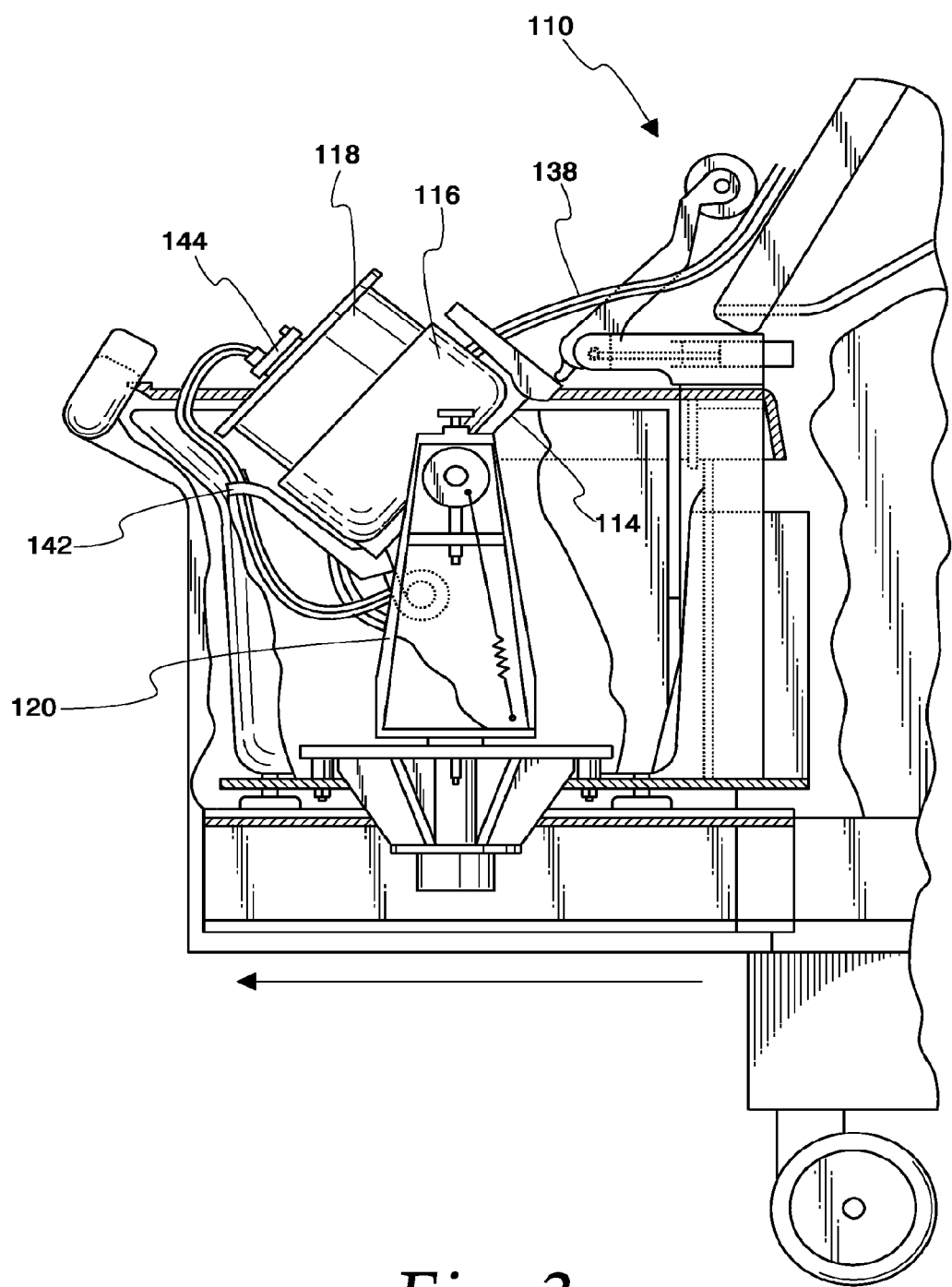
FIG. 3 is a side elevational view, with portions broken away and in section, of the system shown in FIG. 2, with the bowl and spool shown in an upright position for receiving a blood separation chamber.

As noted above, lipid detectors according to the present disclosure are not limited to use in combination with the spinning membrane separator system 10 of FIG. 1, but may be employed in other types of blood processing systems. For example, FIGS. 2 and 3 show a centrifugal blood processing system 110 which may incorporate a lipid detector according to the present disclosure for detecting the presence or concentration of lipids in separated plasma, as described above with regard to the system 10 of FIG. 1.

The present subject matter also has additional utility. According to another aspect of the present disclosure, the system 110 may employ a lipid detector in combination with an interface controller 112 (FIGS. 9 and 10) for improved lipid and interface detection capabilities. The illustrated system 110 shares many centrifuge design aspects with a system currently marketed as the AMICUS® separator by Fenwal, Inc. of Lake Zurich, Ill., as described in greater detail in U.S. Pat. No. 5,868,696, which is hereby incorporated herein by reference. The system 110 can be used for processing various fluids, but is particularly well suited for processing whole blood, blood components, or other suspensions of biological cellular materials.

While interface control and optical detection principles will be described herein with reference to one particular system 110 and centrifuge assembly 114, it should be understood that these principles may be employed with other fluid processing systems (e.g., other centrifugal blood separation systems and centrifuges) without departing from the scope of the present disclosure.

A. The Centrifuge Assembly

The system 110 includes a centrifuge assembly 114 used to centrifugally separate blood components. The system 110 may be programmed to separate blood into a variety of components (e.g., platelet concentrate, platelet-rich plasma, and red cells). It may be used for platelet collection, therapeutic plasma exchange, red cell exchange, red cell or plasma collection, or other blood processing applications. For illustrative purposes only, a platelet collection procedure and a therapeutic plasma exchange procedure will be described herein. However, the principles described and claimed herein may be employed with other blood separation procedures without departing from the scope of the present disclosure.

The illustrated centrifuge assembly 114 shares certain design aspects with the one shown in U.S. Pat. No. 5,316,667 to Brown et al., which is incorporated herein by reference. The illustrated centrifuge assembly, which is shown for purposes of illustration and not limitation, comprises a bowl 116 and a spool 118. In one embodiment, the bowl 116 and spool 118 are pivoted on a yoke 120 between an operating position (FIG. 2) and a loading/unloading position (FIG. 3). Other methods of accessing the bowl 116 and the spool 118 may also be employed without departing from the scope of the present disclosure. The present subject matter may be used with centrifuges that do not employ such a spool and bowl, such as molded centrifuge chambers, centrifuge bowls with preformed processing chamber slots, or other designs.

When in the loading/unloading position, the spool 118 can be opened by movement at least partially out of the bowl 116, as FIG. 3 shows. In this position, the operator wraps a flexible blood separation chamber 122 (see FIG. 4) about the spool 118. Closure of the spool 118 and bowl 116 encloses the chamber 122 between the inner surface of the bowl 116 and the outer surface of the spool 118 (which collectively define the fluid processing region in which the chamber 122 is received) for processing. When closed, the spool 118 and bowl 116 are pivoted into the operating position of FIG. 2 for rotation about a rotational axis.

B. The Blood Separation Chamber

Figure 5:
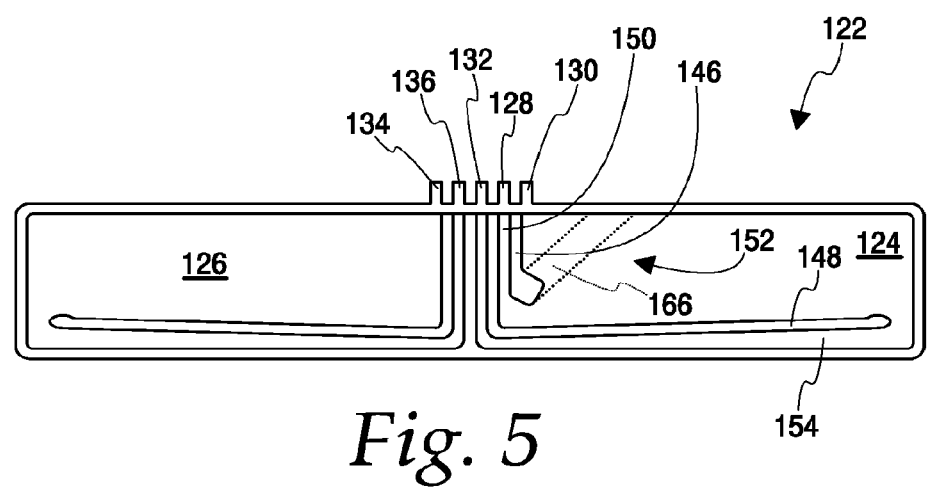
FIG. 5 is a plan view of the blood separation chamber shown in FIG. 4, out of association with the spool.

The blood separation chamber 122 can be variously constructed. FIG. 5 shows a representative embodiment.

The chamber 122 shown in FIG. 5 allows for either single- or multi-stage processing. When used for multi-stage processing of whole blood, a first stage 124 separates whole blood into first and second components. Depending on the nature of the separation procedure, one of the components may be transferred into a second stage 126 for further processing.

Figure 4:
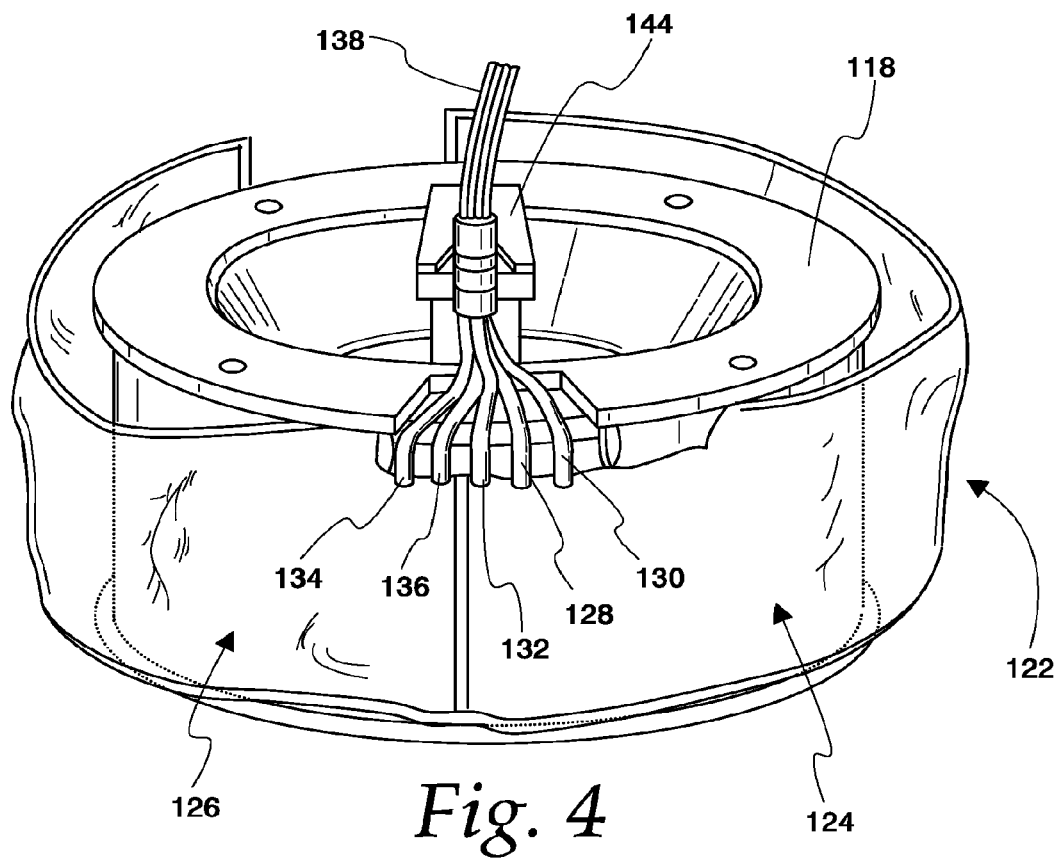
FIG. 4 is a top perspective view of the spool of the centrifuge assembly shown in FIG. 3 in its upright position and carrying the blood separation chamber.

As FIGS. 4 and 5 best show, there are three ports 128, 130, and 132 associated with the first stage 124. Depending on the particular blood processing procedure, the ports may have different functionality but, in an exemplary procedure, the port identified at 132 may be used for conveying blood (which may include anticoagulant) from a blood source or donor into the first stage 124. During such a procedure, the other two ports 128 and 130 may serve as outlet ports for separated blood components exiting the first stage 124. For example, the first outlet port 130 may convey a low density blood component from the first stage 124, while the second outlet port 128 may convey a high density blood component from the first stage 124.

In a method of carrying out single-stage processing, one of the separated components is returned to the donor, while the other is removed from the first stage 124 and stored. For example, when carrying out a therapeutic plasma exchange procedure, whole blood in the first stage 124 is separated into cellular components (i.e., a high density red blood cell component) and substantially cell-free plasma (i.e., a low density component). The plasma is removed from the first stage 124 via the first outlet port 130 for collection and storage, while the cellular components are removed from the first stage 124 via the second outlet port 128 and returned to the donor or patient. Alternatively, rather than collecting and storing the plasma, it may instead be discarded after separation or treated by a secondary device and returned to the donor or patient.

If multi-stage processing is required, for example in a platelet collection procedure, one of the components (platelet-rich plasma) will be transferred from the first stage 124 to the second stage 126 via a port 134 associated with the second stage 126. The component transferred to the second stage 126 is further fractionated into sub-components such as plasma and platelet concentrate, with one of the sub-components (plasma in one embodiment) being removed from the second stage 126 via an outlet port 136 and the other sub-component (platelet concentrate in one embodiment) remaining in the second stage 126. In the illustrated embodiment, the ports 128, 130, 132, 134, and 136 are arranged side-by-side along the top transverse edge of the chamber 122.

While the same ports 128, 130, and 132 of the first stage 124 are used as in the above-described therapeutic plasma exchange procedure, the ports 128 and 132 may have different functionality in a multi-stage separation procedure. In the method of multi-stage operation for platelet collection, blood enters the first stage 124 via the port 128 and is separated into red blood cells (i.e., the high density blood component) and platelet-rich plasma (i.e., the low density blood component). The red blood cells are returned to the donor (via the port 132), while the platelet-rich plasma is conveyed out of the first stage 124 (via the first outlet port 130) and into the second stage 126 (via the inlet port 134). In the second stage 126, the platelet-rich plasma is separated into platelet-poor plasma and platelet concentrate. The platelet-poor plasma is removed from the second stage 126 (via the outlet port 136), leaving platelet concentrate in the second stage 126 for eventual resuspension and transfer to one or more storage containers.

As best shown in FIG. 4, a tubing umbilicus 138 is attached to the ports 128, 130, 132, 134, and 136. The umbilicus 138 interconnects the rotating first and second stages 124 and 126 with each other and with pumps and other stationary components located outside the rotating components of the centrifuge assembly 114 (see FIGS. 2 and 3). As FIG. 2 shows, a non-rotating (zero omega) holder 140 holds the upper portion of the umbilicus 138 in a non-rotating position above the spool 118 and bowl 116. A holder 142 on the yoke 120 rotates the mid-portion of the umbilicus 138 at a first (one omega) speed about the suspended spool 118 and bowl 116. Another holder 144 (FIGS. 3 and 4) mounts the lower end of the umbilicus 138 to the centrifuge assembly 114. The inherent strength of the umbilicus 138 causes the centrifuge assembly 114 to rotate at a second speed twice the one omega speed (the two omega speed). This known relative rotation of the umbilicus 138 keeps it from accumulating twisting, in this way avoiding the need for rotating seals. In an alternative embodiment, rather than the holder 142 rotating the umbilicus 138 to turn the centrifuge assembly 114, a gear system may be employed to rotate the umbilicus 138 and/or the centrifuge assembly 114 separately. It should be noted that the present subject matter can also be employed in centrifuges using rotating seals, and is not limited to use in a sealless centrifuge system.

As FIG. 5 shows, a first interior seal 146 is located between the low density outlet port 130 and the high density outlet port 128. A second interior seal 148 is located between the high density outlet port 128 and the blood inlet port 132. The interior seals 146 and 148 form a fluid passage 150 (an inlet for whole blood in an exemplary platelet collection procedure or an outlet for high density blood components in an exemplary therapeutic plasma exchange procedure) and a low density collection region 152 in the first stage 124. The second seal 148 also forms a fluid passage 154 (an outlet for high density blood components in an exemplary platelet collection procedure or a blood inlet in an exemplary therapeutic plasma exchange procedure) in the first stage 124.

In a platelet collection procedure, the fluid passage 150 channels blood into the first stage 124, where it separates into an optically dense layer 156 (FIG. 6), which forms as larger and/or heavier blood particles move under the influence of centrifugal force toward the high-G (outer) wall 162. The optically dense layer 156 will include red blood cells (and, hence, may be referred to herein as the "RBC layer") but, depending on the speed at which the assembly 114 is rotated, other cellular components (e.g., larger white blood cells) may also be present in the RBC layer 156.

Rather than flowing blood into the first stage 124 by the fluid passage 150 (as in a platelet collection procedure), blood enters the first stage 124 by the fluid passage 154 in a therapeutic plasma exchange procedure, but is still separated into an RBC layer 156. In comparison to a platelet collection procedure, the centrifuge assembly 114 rotates at a higher speed during a therapeutic plasma exchange procedure, creating a stronger separation field in the first stage 124. As a result of the stronger separation field, additional cellular components, namely white blood cells and platelets, will be present in a greater quantity in the RBC layer 156.

In both cases, the movement of the component(s) of the RBC layer 156 displaces less dense blood components radially toward the low-G (inner) wall 164, forming a second, less optically dense layer 158. In an exemplary platelet collection procedure, the less optically dense layer 158 includes platelet-rich plasma (and, hence, will be referred to herein as the "plasma layer"). In an exemplary therapeutic plasma exchange procedure, the less optically dense layer 158 includes substantially cell-free plasma. However, depending on the speed at which the centrifuge assembly 114 is rotated and the length of time that the blood is resident in the centrifuge assembly, other components (e.g., smaller white blood cells) may also be present in the plasma layer 158.

The transition between the RBC layer 156 and the plasma layer 156 is generally referred to as the interface 160 (FIG. 6). Platelets and white blood cells (which have a density greater than plasma and usually less than red blood cells) typically occupy this transition region, although that also varies with centrifuge speed and residence time, as is well known in the technical field.

The location of the interface 160 within the chamber 122 can dynamically shift during blood processing, as FIGS. 7 and 8 show. If the location of the interface 160 is too high (that is, if it is too close to the low-G wall 164 and the removal port 130, as FIG. 7 shows), cellular components can spill over and into the low density collection region 152, potentially adversely affecting the quality of the low density components (typically plasma). On the other hand, if the location of the interface 160 is too low (that is, if it resides too far away from the low-G wall 164, as FIG. 8 shows), the collection efficiency of the system 110 may be impaired.

In the illustrated embodiment, as FIG. 6 shows, a ramp 166 extends from the high-G wall 162 of the bowl 116 at an angle "A" across the low density collection region 152. The angle "A," measured with respect to the axis of the first outlet port 130 is about 25° in one embodiment. FIG. 6 shows the orientation of the ramp 166 when viewed from the low-G wall 164 of the spool 118. FIG. 5 shows, in phantom lines, the orientation of the ramp 166 when viewed from the high-G wall 162 of the bowl 116.

Further details of the angled relationship of the ramp 166 and the first outlet port 130 can be found in U.S. Pat. No. 5,632,893 to Brown et al., which is incorporated herein by reference.

The ramp 166 forms a tapered wedge that restricts the flow of fluid toward the first outlet port 130. The top edge of the ramp 166 extends to form a constricted passage 168 along the low-G wall 164. The plasma layer 158 must flow through the constricted passage 168 to reach the first outlet port 130.

As FIG. 6 shows, the ramp 166 makes the interface 160 between the RBC layer 156 and the plasma layer 158 more discernible for detection, displaying the RBC layer 156, plasma layer 158, and interface 160 for viewing through a light-transmissive portion of the high-G wall 162 of the chamber 122, as will be described in greater detail below.

Further details of the separation chamber 122 and its operation may be found in U.S. Pat. No. 5,316,667, which is incorporated by reference.

C. The Interface Controller

In one embodiment, the interface controller 112 (FIGS. 9 and 10) includes a first optical sensor system or assembly 170 and a second optical sensor system 172 (FIG. 9) or 172a (FIG. 10) positioned at different locations outside of the centrifuge assembly 114. While the first and second optical sensor systems are described as being used in combination as part of an interface controller 112, they may be used separately without departing from the scope of the present disclosure.

(1) The First Optical Sensor System

The first optical sensor system 170 is oriented to detect the location of the interface 160 the RBC layer 156 and the plasma layer 158 on the ramp 166. If the interface 160 detected by the first optical sensor system 170 is at an improper location (e.g., in the locations of FIG. 7 or 8), the interface controller 112 is functional to correct the location of the interface 160. A suitable first optical sensor system 170 and method of determining the location of an interface 160 are described in U.S. Pat. No. 6,312,607, which is incorporated by reference. Other systems and methods for determining the location of an interface 160 may be employed without departing from the scope of the present disclosure.

In one embodiment, the first optical sensor system 170 shines light through the ramp 166. The light is reflected back to the first optical sensor system 170, which generates one or more signals that are transmitted to an interface processing module 174 (FIGS. 9 and 10), which can determine the location of the interface 160 on the ramp 166 relative to the constricted passage 168.

When the location of the interface 160 on the ramp 166 has been determined, the interface processing module 174 outputs that information to an interface command element or module 176. The interface command module 176 may include a comparator, which compares the interface location output with a desired interface location to generate an error signal. The error signal may take a number of forms but, in one embodiment, may be expressed in terms of a targeted red blood cell percentage value (i.e., the percentage of the ramp 166 which should be occupied by the RBC layer 156).

Figure 9:
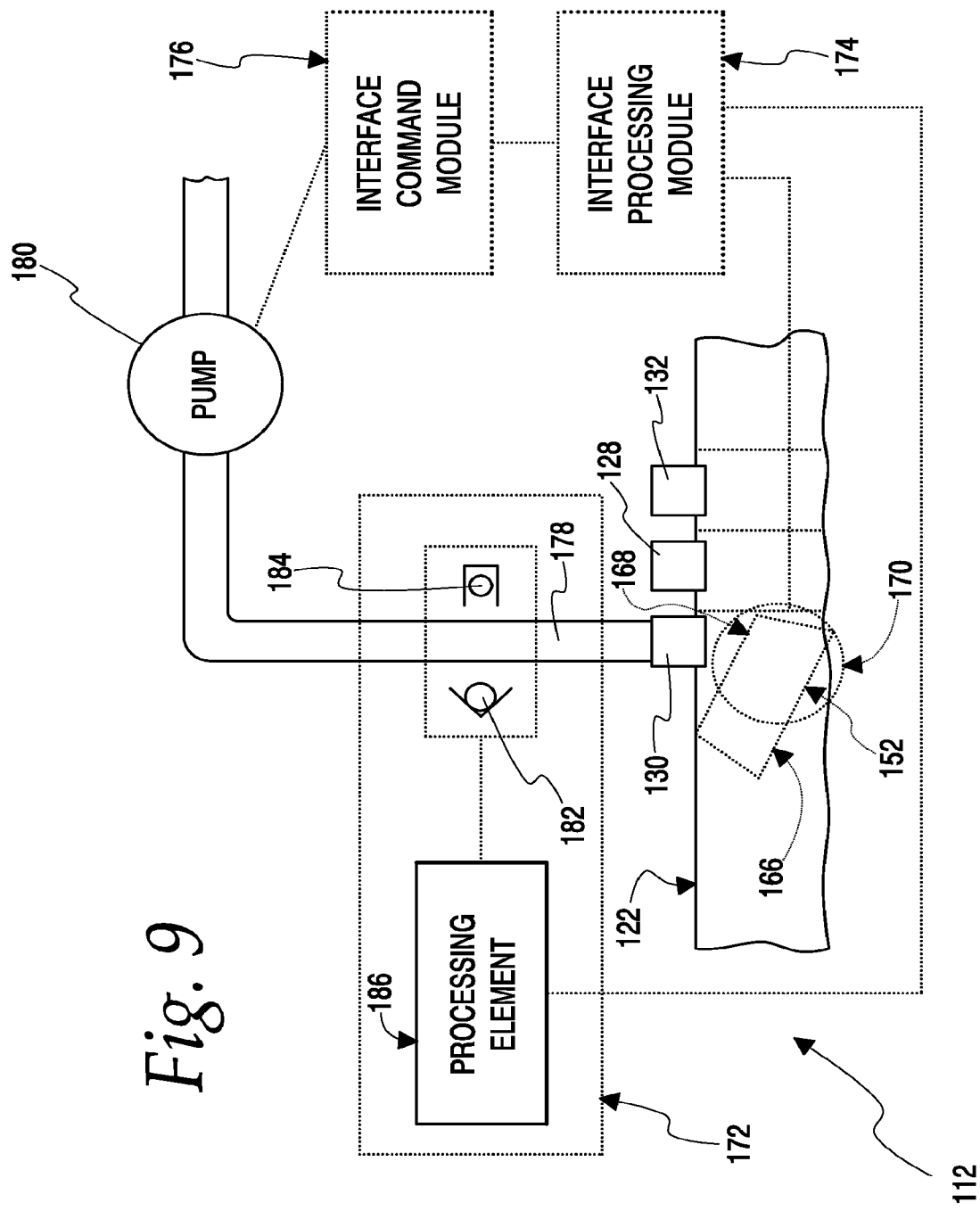
FIG. 9 is a schematic view of an optical sensor assembly, which may form a part of the interface controller.
Figure 10:
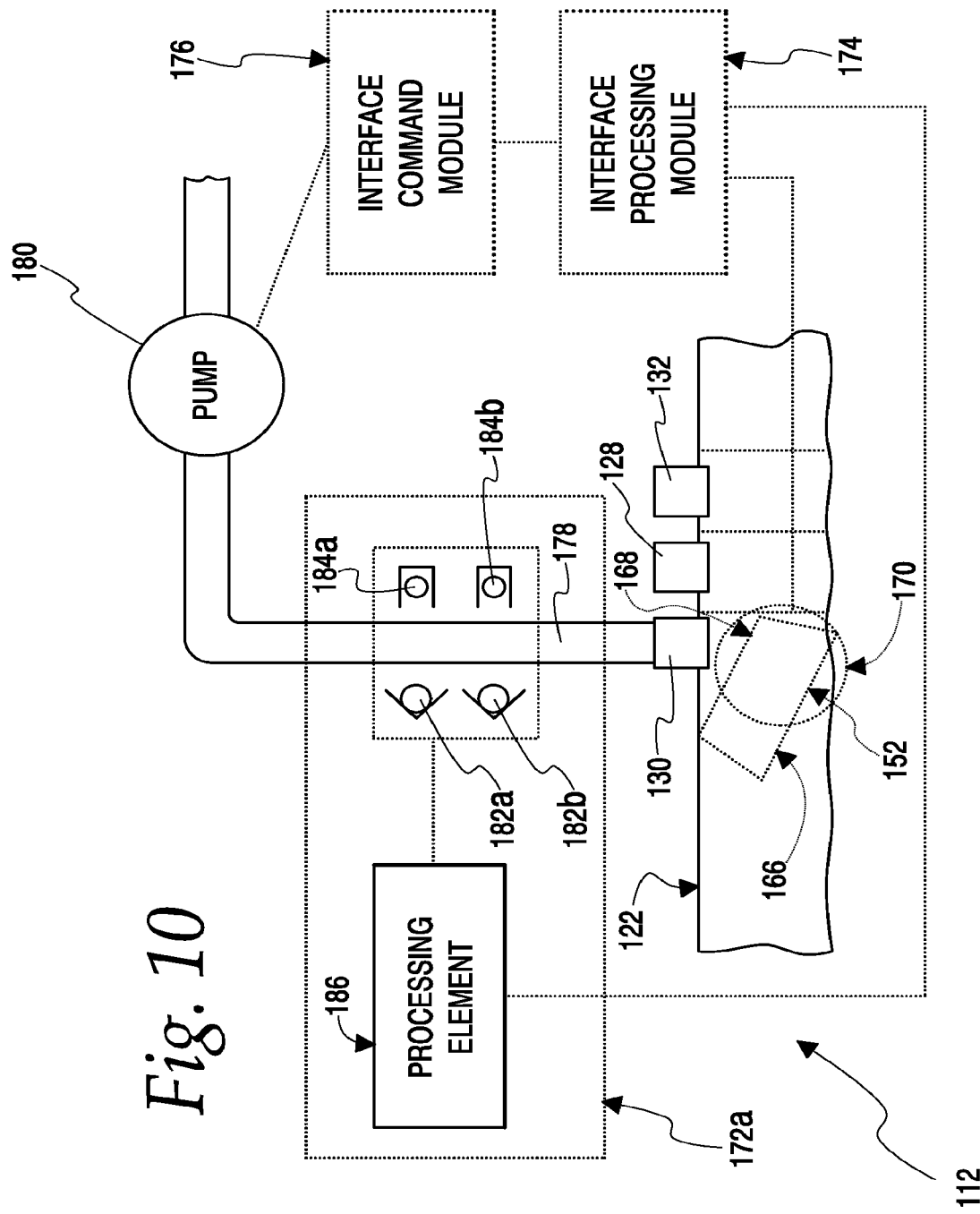
FIG. 10 is a schematic view of an alternative optical sensor assembly, which may form a part of the interface controller.

When the control value is expressed in terms of a targeted red blood cell percentage value, a positive error signal indicates that the RBC layer 156 on the ramp 166 is too large (as FIG. 7 shows). The interface command module 176 generates a signal to adjust an operational parameter accordingly, such as by reducing the rate at which plasma is removed through tubing 178 connected to the first outlet port 130 under action of a pump 178 (FIGS. 9 and 10). The interface 160 moves away from the constricted passage 68 toward the desired control position (as FIG. 6 shows), where the error signal is zero.

A negative error signal indicates that the RBC layer 156 on the ramp 166 is too small (as FIG. 8 shows). The interface command module 176 generates a signal to adjust an operational parameter accordingly, such as by increasing the rate at which plasma is removed through the first outlet port 130. The interface 160 moves toward the constricted passage 168 to the desired control position (FIG. 6), where the error signal is again zero.

(2) The Second Optical Sensor System

The presence of either lipids decreases the light transmissivity of the plasma layer 158, which can result in a miscalculation of the interface location by the first optical sensor system 170. Accordingly, the second optical sensor system 172, 172a may be provided separately to determine whether lipids are present in the plasma layer 158. If so, the second sensor system 172, 172a may cooperate with the interface processing module 174 and the interface command module 176 to adjust the location calculation and response arising from the signals generated by the first optical sensor system 170, as will be described in greater detail herein.

FIG. 9 shows an exemplary second optical sensor system 172, while FIG. 10 illustrates an alternative second optical sensor system 172a that is structurally and functionally similar to the system 172, except as noted below.

The second optical sensor system 172, 172a may be positioned to monitor any light-transmissive portion of the fluid circuit where the plasma layer 158 is present. In the illustrated embodiment, the second optical sensor system 172, 172a is positioned to monitor the tubing 178 connected to the first outlet port 130 of the blood separation chamber 122, so as to monitor plasma exiting the first stage 124. When incorporated into other blood processing systems, the second optical sensor system may be positioned in other locations, e.g., either inside or outside of the centrifuge assembly (or whatever device is used to separate plasma from the blood) or partially inside and partially outside of the centrifuge assembly (or whatever device is used to separate plasma from the blood).

In the illustrated embodiments of FIGS. 9 and 10, the second optical sensor system 172, 172a includes one or more light sources 182, 182a, 182b and one or more light detectors 184, 184a, 184b positioned and oriented to receive at least a portion of light emitted by the light source(s). For example, in one embodiment, each light source includes an associated light detector on the opposite side of the tubing 178. In other embodiments, the light detectors may be positioned at an angle with respect to the associated light sources and/or there may be a different number of light sources and light detectors.

Each light source 182, 182a, 182b shines light through the tubing 178, to be at least partially received by the associated light detector(s) 184, 184a, 184b. According to the above description of the lipid detector 40 of FIG. 1, each light source may be configured to emit blue and/or ultraviolet light to detect the presence of lipids in the separated plasma.

The blue and/or ultraviolet light passes through the tubing 178 and plasma and is at least partially received by the associated light detector(s) 184, 184a, 184b. The light detector or detectors (which may comprise photodiodes in one embodiment) generate a signal that is received by a processor or processing element 186 of the second optical sensor system 172, 172a. In an alternative embodiment, the signal(s) from the light detector(s) may be directly transmitted to a different component of the interface controller 112, such as the interface processing module 174. In yet another embodiment, the processing element 186 is incorporated into a different component of the interface controller 112, such as the interface processing module 174.

The processing element 186 analyzes the signal(s) from the light detector(s) to determine the lipid content of the separated plasma. This analysis may be carried out by the processing element 186 in any of a variety of ways, such as in the way described above with respect to the embodiment of FIG. 1. After analyzing the signal(s), the processing element 186 generates an output indicative of the lipid content or concentration of the plasma in the tubing 178. In one embodiment, which is shown in FIGS. 9 and 10, the output from the processing element 186 is passed to the interface processing module 174 for use in locating and controlling the position of the interface 160 on the ramp 166. As noted above, the light transmissivity of the plasma layer 158 will vary according to the concentration of lipids in the plasma, which depends upon the physiology or morphology of the individual donor. Lipemic plasma has an optical density that differs significantly from saline or non-lipemic plasma. As a result, the presence of plasma on the ramp 166 carrying high concentrations of lipids diminishes the magnitude of the sensed voltage signals, independent of and unrelated to changes in the physical dimensions of the interface. Accordingly, the first optical sensor system 170 may, in that situation, have reduced accuracy in monitoring the location of the interface 160.

As shown in FIGS. 9 and 10, the processing element 186 of the second optical sensor system 172, 172a may be associated with the interface processing element or module 174, which is, in turn, associated with the interface command element or module 176. The illustrated interface command module 174 controls the operation of the pump 180 associated with the tubing 178 for removing plasma from the blood separation chamber 122. Accordingly, signals collected and processed by the processing element 186 of the second optical sensor system 172, 172a may be considered or factored in when determining the location of the interface 160 and/or taking corrective action to reposition the interface 160 (e.g., by changing the rate of operation of the pump 180). A system and method of employing two separate sensor assemblies to determine and control the location of an interface is described in U.S. patent application Ser. No. 13/021,346 to Foley et al., which is incorporated herein by reference. As in the present disclosure, the system and method of U.S. patent application Ser. No. 13/021,346 uses a lipid sensor to correct or improve the operation of a first sensor, so its system and method may be practiced with the second optical sensor system 172, 172a to more accurately determine the location of the interface between separated plasma and red blood cells in a blood separation chamber.

While the foregoing description has related primarily to embodiments in which a lipid detector is employed in association with outlet tubing of a blood separation device, it should be understood that lipid detectors according to the present disclosure may be employed in other locations where separated plasma would be present. For example, a lipid detector may be configured and oriented to shine blue and/or ultraviolet light into a separation device, which may be achieved by locating and orienting the lipid detector similar to that of the first optical sensor system 170 described above and shown in FIGS. 9 and 10. In another example, a lipid detector may be configured and oriented to shine blue and/or ultraviolet light into a plasma storage container 38 (FIG. 1).

Aspects of the present subject matter described above may be beneficial alone or in combination with one or more other aspects. Without limiting the foregoing description, in accordance with one aspect of the subject matter herein, there is provided an optical sensor system for use in combination with a blood separator having a plasma flow path for the flow of separated plasma. The optical sensor system includes a blue and/or ultraviolet light source configured to pass a blue and/or ultraviolet light through plasma in the plasma flow path. The system also include a light detector configured to receive at least a portion of the blue and/or ultraviolet light passing through the plasma and generate a signal indicative of lipid content in the plasma in the plasma flow path.

In accordance with another aspect which may be used or combined with the preceding aspect, the blue light wavelength is substantially in the range of about 450-510 nm.

In accordance with another aspect which may be used or combined with any of the preceding aspects, the ultraviolet light wavelength is substantially in the range of about 300-400 nm.

In accordance with another aspect which may be used or combined with any of the preceding aspects, the light source emits blue light and ultraviolet light.

In accordance with another aspect which may be used or combined with any of the preceding aspects, a further light source is configured to pass light of a wavelength substantially in the range of about 550-580 nm through plasma in the plasma flow path and a light detector is configured to receive at least a portion of the further light passing through the plasma and generate a signal indicative of hemoglobin content.

In accordance with another aspect which may be used or combined with any of the preceding aspects, the light source includes a plurality of separate light sources and/or the light detector includes a plurality of separate light detectors.

In accordance with another aspect, there is provided a blood processing system. The blood processing system includes a blood separator with a fluid processing region, which is configured to separate plasma from blood. The system also includes a plasma flow path communicating with the fluid processing region for removing plasma therefrom. An optical sensor system of the blood processing system includes a blue and/or ultraviolet light source configured to pass a blue and/or ultraviolet light through separated plasma in the plasma flow path. The optical sensor system also includes one or more light detectors configured to receive at least a portion of the blue and/or ultraviolet light passing through the plasma and generate a signal indicative of lipid content in the separated plasma.

In accordance with another aspect which may be used or combined with the preceding aspect, the blue light wavelength is substantially in the range of about 450-510 nm.

In accordance with another aspect which may be used or combined with any of the preceding two aspects, the ultraviolet light wavelength is substantially in the range of about 300-400 nm.

In accordance with another aspect which may be used or combined with any of the preceding three aspects, the light source emits blue light and ultraviolet light.

In accordance with another aspect which may be used or combined with any of the preceding four aspects, a controller is configured to generate an output indicative of an elevated lipid content when less than 50% of the light emitted by the light source is detected by the one or more light detectors.

In accordance with another aspect which may be used or combined with any of the preceding five aspects, a further light source is configured to pass light of a wavelength substantially in the range of about 550-580 nm through plasma in the plasma flow path. A light detector is configured to receive at least a portion of the further light passing through the plasma and generate a signal indicative of hemoglobin content.

In accordance with another aspect which may be used or combined with any of the preceding six aspects, the light source includes a plurality of separate light sources and/or the light detector includes a plurality of separate light detectors.

In accordance with another aspect, there is provided a method for separating blood into plasma and other blood components. The method includes separating plasma from blood and passing a blue and/or ultraviolet light through the separated plasma. At least a portion of the blue and/or ultraviolet light is received after passing through the separated plasma and a signal is generated based on the amount of blue and/or ultraviolet light passing through the plasma. The signal is indicative of lipid content in the separated plasma.

In accordance with another aspect which may be used or combined with the preceding aspect, the blue light wavelength is substantially in the range of about 450-510 nm.

In accordance with another aspect which may be used or combined with any of the preceding two aspects, the ultraviolet light wavelength is substantially in the range of about 300-400 nm.

In accordance with another aspect which may be used or combined with any of the preceding three aspects, the light source emits blue light and ultraviolet light.

In accordance with another aspect which may be used or combined with any of the preceding four aspects, a controller is configured to generate an output indicative of an elevated lipid content when less than 50% of the light emitted by the light source is detected by the one or more light detectors.

In accordance with another aspect which may be used or combined with any of the preceding five aspects, light having a wavelength substantially in the range of about 550-580 nm is passed through the separated plasma. At least a portion of the 550-580 nm wavelength light is received after passing through the separated plasma. A signal is generated based on the amount of the 550-580 nm wavelength light that passes through the plasma, with the signal being indicative of hemoglobin content in the separated plasma.

In accordance with another aspect which may be used or combined with any of the preceding six aspects, the light source includes a plurality of separate light sources and/or the light detector includes a plurality of separate light detectors.

In accordance with another aspect which may be used or combined with any of the preceding seven aspects, the light is passed through the separated plasma by a plurality of separate light sources and/or received by a plurality of separate light detectors after passing through the separated plasma.

In accordance with another aspect, the method of any of the preceding eight aspects is performed using the system of any of the first thirteen aspects.

In accordance with another aspect, an optical sensor system is provided for use in combination with a blood separator including a plasma flow path for the flow of separated plasma. The optical sensor system includes a first light source configured to pass a first light through plasma in the plasma flow path, the first light being of a selected first wavelength that is significantly absorbed by hemoglobin in the plasma. A second light source is configured to pass a second light through plasma in the plasma flow path, with the second light being of a selected wavelength that is not significantly absorbed by hemoglobin, but is significantly absorbed by lipids in the plasma.

In accordance with another aspect which may be used or combined with the preceding aspect, the first wavelength is substantially between about 550 and 580 nm.

In accordance with another aspect which may be used or combined with any of the preceding two aspects, the second wavelength is substantially between about 450 and 510 nm and/or substantially between about 300 and 400 nm.

In accordance with another aspect which may be used or combined with any of the preceding three aspects, the optical sensor system is used in combination with a blood separator.

In accordance with another aspect which may be used or combined with any of the preceding four aspects, at least one light detector is configured to receive at least a portion of the first and/or second light passing through the plasma and generate a responsive signal based at least in part on the amount of first and/or second light passing through the plasma.

In accordance with another aspect which may be used or combined with any of the preceding five aspects, a processor is operably associated with the at least one light detector to generate an output indicative of the content of lipids and/or hemoglobin in the plasma in the plasma flow path.

In accordance with another aspect which may be used or combined with the preceding aspect, the processor is configured to generate an output indicative of an elevated lipid content when at least 50% of the second light emitted by the second light source is absorbed by the plasma in the plasma flow path.

In accordance with another aspect which may be used or combined with any of the preceding seven aspects, the second light substantially comprises blue light and/or ultraviolet light.

In accordance with another aspect which may be used or combined with any of the preceding eight aspects, the second light comprises light having a wavelength of essentially about 470 nm and/or about 380 nm.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method of separating blood into plasma and other blood components, comprising:
    separating plasma from blood in a blood separator;
    removing at least a portion of the separated plasma from the blood separator via a plasma flow path;
    passing a blue and/or ultraviolet light through the separated plasma in the blood separator or in the plasma flow path;
    receiving at least a portion of said blue and/or ultraviolet light after passing through the separated plasma;
    generating a signal based on the amount of blue and/or ultraviolet light passing through the separated plasma indicative of lipid content in the separated plasma;
    determining the lipid content of the separated plasma by comparing the difference between the signal and a reference signal representing receipt of all or a preselected amount of the blue and/or ultraviolet light; and
    generating an output indicative of the lipid content in the separated plasma.

2. The method of separating blood of claim 1 in which the blue and/or ultraviolet light comprises blue light having a wavelength substantially in the range of about 450-510 nm.

3. The method of separating blood of claim 2 in which said generating a signal includes generating a signal indicative of an elevated lipid content when less than 50% of the blue light passes through the separated plasma.

4. The method of separating blood of claim 1 in which the blue and/or ultraviolet light comprises ultraviolet light having a wavelength substantially in the range of about 300-400 nm.

5. The method of separating blood of claim 1, further including
    passing light of a wavelength substantially in the range of about 550-580 nm through the separated plasma, receiving at least a portion of the 550-580 nm wavelength light after passing through the separated plasma, and generating a signal based on the amount of the 550-580 nm wavelength light passing through the separated plasma indicative of hemoglobin content in said separated plasma.

6. The method of separating blood of claim 1, in which the blue and/or ultraviolet light is passed through the separated plasma by a plurality of separate light sources and/or received by a plurality of separate light detectors after passing through the separated plasma.

7. The method of separating blood of claim 6, wherein the plurality of separate light sources emit light having the same wavelength.

8. The method of separating blood of claim 6, wherein the plurality of separate light sources emit light having different wavelengths.

9. The method of separating blood of claim 6, wherein
each one of the plurality of separate light detectors generates a signal indicative of lipid content in the separated plasma, and
said generating a signal includes aggregating the signals generated by the plurality of separate light detectors into a single signal.

10. The method of separating blood of claim 1, wherein the blood separator includes a spinning membrane.

11. The method of separating blood of claim 1, wherein the blood separator includes a centrifuge assembly.

12. The method of separating blood of claim 1, wherein the blue and/or ultraviolet light is passed through the plasma flow path and received at a location opposite a location from which the blue and/or ultraviolet light is emitted.

13. The method of separating blood of claim 1, wherein the blue and/or ultraviolet light is passed through the plasma flow path and received at a location positioned at an angle with respect to a location from which the blue and/or ultraviolet light is emitted.

14. The method of separating blood of claim 1, further comprising determining the location of an interface between separated blood components in the blood separator, wherein the determination of the location of the interface is based at least in part on the lipid content of the separated plasma.

15. The method of separating blood of claim 1, further comprising quantifying platelets present in the separated plasma, wherein the quantification of platelets present in the separated plasma is based at least in part on the lipid content of the separated plasma.

16. The method of separating blood of claim 1, further comprising monitoring the separated plasma for elevated hemoglobin content, wherein said passing the blue and/or ultraviolet light through the separated plasma, said receiving at least a portion of said blue light, and said generating a signal are performed only upon the detection of elevated hemoglobin content in the separated plasma.

17. The method of separating blood of claim 1, further comprising
determining whether the separated plasma has an elevated lipid content based at least in part on the signal,
detecting an elevated hemoglobin content in the separated plasma, and
generating an alarm indicative of elevated hemoglobin content in the separated plasma only if the separated plasma does not have an elevated lipid content.

18. The method of separating blood of claim 1, further comprising flowing said at least a portion of the separated plasma into a plasma storage container, wherein said passing a blue and/or ultraviolet light through the separated plasma in the blood separator or in the plasma flow path further comprises passing blue and/or ultraviolet light through the separated plasma in the plasma storage container.

* * * * *